United States Patent
Verleur et al.

(10) Patent No.: US 10,893,704 B2
(45) Date of Patent: Jan. 19, 2021

(54) VAPORIZER

(71) Applicant: VMR Products LLC, Miami, FL (US)

(72) Inventors: Jan Andries Verleur, Miami Beach, FL (US); Dan Recio, Miami Beach, FL (US); Zhiyuan Liu, Miami, FL (US); Hans Verleur, El Dorado, CA (US)

(73) Assignee: VMR Products, LLC, San Francisco, CA (US)

(*) Notice: Subject to any disclaimer, the term of this patent is extended or adjusted under 35 U.S.C. 154(b) by 25 days.

(21) Appl. No.: 15/839,305

(22) Filed: Dec. 12, 2017

(65) Prior Publication Data

US 2018/0160738 A1 Jun. 14, 2018

Related U.S. Application Data

(60) Provisional application No. 62/433,000, filed on Dec. 12, 2016, provisional application No. 62/485,195, filed on Apr. 13, 2017.

(51) Int. Cl.
*A24F 47/00* (2020.01)
*A61M 11/04* (2006.01)
*A61M 15/00* (2006.01)

(52) U.S. Cl.
CPC ......... *A24F 47/008* (2013.01); *A61M 11/042* (2014.02); *A61M 15/002* (2014.02); *A61M 15/0026* (2014.02); *A61M 2205/50* (2013.01); *A61M 2205/502* (2013.01); *A61M 2205/505* (2013.01); *A61M 2205/8206* (2013.01); *A61M 2205/8237* (2013.01); *A61M 2205/8243* (2013.01); *A61M 2209/045* (2013.01); *A61M 2209/06* (2013.01)

(58) Field of Classification Search
None
See application file for complete search history.

(56) References Cited

U.S. PATENT DOCUMENTS

| | | | | |
|---|---|---|---|---|
| 1,706,846 A | * | 3/1929 | Fisher | F24H 3/0411 |
| | | | | 126/90 A |
| 1,981,916 A | * | 11/1934 | Huntley | F24F 6/12 |
| | | | | 219/473 |
| 2,088,717 A | * | 8/1937 | Nowak | A61M 11/041 |
| | | | | 128/203.27 |
| 2,817,000 A | * | 12/1957 | Scheid | A45D 20/08 |
| | | | | 392/383 |
| 3,192,167 A | * | 6/1965 | Ogawa | B05B 3/001 |
| | | | | 261/156 |
| 3,511,236 A | * | 5/1970 | Conlin | A61H 33/12 |
| | | | | 128/203.27 |

(Continued)

FOREIGN PATENT DOCUMENTS

| | | |
|---|---|---|
| CA | 2789362 C | 5/2014 |
| CN | 201104488 Y | 8/2008 |

(Continued)

*Primary Examiner* — Thor S Campbell
(74) *Attorney, Agent, or Firm* — Mintz Levin Cohen Ferris Glovsky and Popeo, P.C.

(57) ABSTRACT

A vaporizer is disclosed. The vaporizer includes a body, an air pump, a heating block, a filling chamber, an air channel, and a control panel. The control panel is in electrical communication with the battery, the air pump, and the heating block and is configured to control a speed of the air pump and a temperature of the heating block.

14 Claims, 15 Drawing Sheets

(56) References Cited

U.S. PATENT DOCUMENTS

| | | | |
|---|---|---|---|
| 3,749,092 A * | 7/1973 | Williams | A61H 33/12 604/24 |
| 3,873,806 A * | 3/1975 | Schossow | F24F 6/025 392/402 |
| 4,190,052 A * | 2/1980 | McCarthy | A61H 33/12 392/403 |
| 4,399,349 A * | 8/1983 | Deming | A45D 19/16 128/203.17 |
| 4,571,485 A * | 2/1986 | Spector | F24F 3/12 239/136 |
| 4,764,660 A * | 8/1988 | Swiatosz | F41H 9/06 219/505 |
| 4,764,661 A * | 8/1988 | Rautio | F24F 6/025 392/402 |
| 4,810,854 A * | 3/1989 | Jursich | F24F 6/18 392/405 |
| 4,818,843 A * | 4/1989 | Swiatosz | A62B 27/00 392/397 |
| 5,175,791 A | 12/1992 | Muderlak et al. | |
| 5,381,509 A * | 1/1995 | Mills | F24C 1/14 392/376 |
| 5,825,975 A * | 10/1998 | Privas | B05B 7/1686 392/404 |
| 5,991,507 A * | 11/1999 | Bencsits | A61L 9/037 261/99 |
| 6,865,341 B1 * | 3/2005 | Hurley | F41H 9/06 392/386 |
| 7,043,147 B1 * | 5/2006 | Friedheim | F22B 1/287 122/476 |
| 7,302,170 B1 * | 11/2007 | Chen | F22B 1/282 392/398 |
| 7,367,334 B2 * | 5/2008 | Faison, Jr. | A61M 11/041 128/203.12 |
| 8,464,867 B2 | 6/2013 | Holloway et al. | |
| 8,917,980 B2 * | 12/2014 | Scully | A63J 5/025 392/397 |
| 8,967,382 B2 | 3/2015 | Liu | |
| 9,078,472 B2 | 7/2015 | Liu | |
| 9,089,166 B1 | 7/2015 | Scatterday | |
| 9,167,850 B2 | 10/2015 | Liu | |
| 9,198,464 B2 | 12/2015 | Liu | |
| 9,254,005 B2 | 2/2016 | Liu | |
| 9,301,545 B2 | 4/2016 | Li et al. | |
| 9,302,825 B2 | 4/2016 | Liu | |
| 9,415,929 B2 | 8/2016 | Liu | |
| 9,572,372 B2 | 2/2017 | Liu | |
| 9,861,135 B2 | 1/2018 | Chen | |
| 9,943,113 B2 | 4/2018 | Liu | |
| 10,195,345 B2 | 2/2019 | Senior et al. | |
| 10,232,283 B2 * | 3/2019 | Liao | A63J 5/025 |
| 2002/0071664 A1 * | 6/2002 | Aronie | A63H 33/28 392/399 |
| 2002/0078951 A1 | 6/2002 | Nichols et al. | |
| 2002/0154903 A1 * | 10/2002 | Glucksman | F24F 6/18 392/403 |
| 2002/0158351 A1 | 10/2002 | Wohrle | |
| 2003/0063901 A1 * | 4/2003 | Gu | B01D 1/0082 392/394 |
| 2004/0182855 A1 * | 9/2004 | Centanni | A61L 2/07 219/628 |
| 2004/0211418 A1 | 10/2004 | Shayan | |
| 2005/0019026 A1 * | 1/2005 | Wang | B01D 1/0082 392/389 |
| 2005/0279353 A1 | 12/2005 | McCoy | |
| 2009/0192443 A1 | 7/2009 | Collins, Jr. | |
| 2010/0166396 A1 * | 7/2010 | Xu | D06F 73/00 392/394 |
| 2010/0260491 A1 * | 10/2010 | Pitz | A01M 1/2061 392/390 |
| 2011/0030706 A1 * | 2/2011 | Gibson | A61M 11/041 131/328 |
| 2011/0077572 A1 | 3/2011 | Thomas | |
| 2012/0255546 A1 | 10/2012 | Goetz et al. | |
| 2012/0261286 A1 | 10/2012 | Holloway et al. | |
| 2012/0269497 A1 * | 10/2012 | Hatten | A61M 11/041 392/386 |
| 2013/0146489 A1 | 6/2013 | Scatterday | |
| 2013/0174842 A1 | 7/2013 | Young et al. | |
| 2014/0000638 A1 | 1/2014 | Sebastian et al. | |
| 2014/0311505 A1 | 10/2014 | Liu | |
| 2015/0013699 A1 | 1/2015 | Ellis | |
| 2015/0108019 A1 | 4/2015 | Liu | |
| 2015/0114410 A1 | 4/2015 | Doster | |
| 2015/0125136 A1 | 5/2015 | Sanchez | |
| 2015/0150308 A1 | 6/2015 | Monsees et al. | |
| 2015/0164138 A1 | 6/2015 | Liu | |
| 2015/0208725 A1 * | 7/2015 | Tsai | A24F 47/008 392/390 |
| 2015/0224268 A1 | 8/2015 | Henry et al. | |
| 2015/0257447 A1 | 9/2015 | Sullivan | |
| 2015/0272211 A1 | 10/2015 | Chung | |
| 2015/0305409 A1 | 10/2015 | Verleur et al. | |
| 2015/0313287 A1 | 11/2015 | Verleur et al. | |
| 2015/0333561 A1 | 11/2015 | Alarcon | |
| 2015/0342258 A1 | 12/2015 | Chen | |
| 2015/0351455 A1 | 12/2015 | Liu | |
| 2016/0015104 A1 | 1/2016 | Edwards et al. | |
| 2016/0091194 A1 | 3/2016 | Liu | |
| 2016/0099592 A1 | 4/2016 | Gatta et al. | |
| 2016/0120218 A1 | 5/2016 | Schennum et al. | |
| 2016/0165952 A1 | 6/2016 | Liu | |
| 2016/0235124 A1 | 8/2016 | Krietzman | |
| 2016/0261021 A1 | 9/2016 | Marion et al. | |
| 2016/0262453 A1 | 9/2016 | Ampolini et al. | |
| 2016/0262456 A1 | 9/2016 | Borkovec et al. | |
| 2016/0262459 A1 | 9/2016 | Monsees et al. | |
| 2016/0295913 A1 | 10/2016 | Guo et al. | |
| 2016/0331913 A1 | 11/2016 | Bourque | |
| 2016/0338412 A1 | 11/2016 | Monsees et al. | |
| 2016/0353805 A1 | 12/2016 | Hawes et al. | |
| 2016/0360790 A1 | 12/2016 | Calfee et al. | |
| 2017/0013875 A1 | 1/2017 | Schennum et al. | |
| 2017/0013876 A1 | 1/2017 | Schennum et al. | |
| 2017/0027221 A1 | 2/2017 | Liu | |
| 2017/0035115 A1 | 2/2017 | Monsees et al. | |
| 2017/0079327 A1 | 3/2017 | Wu et al. | |
| 2017/0099877 A1 | 4/2017 | Worm et al. | |
| 2017/0101256 A1 | 4/2017 | Zeitlin et al. | |
| 2017/0119044 A1 | 5/2017 | Oligschlaeger et al. | |
| 2017/0119060 A1 | 5/2017 | Li et al. | |
| 2017/0181476 A1 | 6/2017 | Li et al. | |
| 2017/0196272 A1 | 7/2017 | Li et al. | |
| 2017/0202265 A1 | 7/2017 | Hawes et al. | |
| 2017/0214261 A1 | 7/2017 | Gratton | |
| 2017/0215479 A1 | 8/2017 | Kies | |
| 2017/0222468 A1 | 8/2017 | Schennum et al. | |
| 2017/0251729 A1 | 9/2017 | Li et al. | |
| 2017/0280770 A1 | 10/2017 | Wang et al. | |
| 2017/0334605 A1 | 11/2017 | Murphy et al. | |
| 2018/0000160 A1 | 1/2018 | Taschner et al. | |
| 2018/0035718 A1 | 2/2018 | Liu | |
| 2018/0117268 A1 | 5/2018 | Selby et al. | |
| 2018/0153219 A1 | 6/2018 | Verleur et al. | |
| 2018/0160738 A1 | 6/2018 | Verleur et al. | |
| 2018/0177234 A1 | 6/2018 | Lee | |
| 2019/0069601 A1 | 3/2019 | Qiu | |
| 2019/0159519 A1 | 5/2019 | Bowen et al. | |

FOREIGN PATENT DOCUMENTS

| | | |
|---|---|---|
| CN | 105249536 A | 1/2016 |
| CN | 105919164 B | 3/2019 |
| EP | 1078600 A2 | 2/2001 |
| EP | 3031338 A1 | 6/2016 |
| EP | 3141489 B1 | 4/2019 |
| KR | 200457340 Y1 | 12/2011 |
| KR | 200464538 | 1/2013 |
| WO | WO-2012091249 A1 | 7/2012 |
| WO | WO-2012134117 A2 | 10/2012 |
| WO | WO-2014067236 A1 | 5/2014 |
| WO | WO-2014117382 A1 | 8/2014 |
| WO | WO-2015013890 A1 | 2/2015 |

(56) References Cited

FOREIGN PATENT DOCUMENTS

| WO | WO-2015070398 A1 | 5/2015 |
|---|---|---|
| WO | WO-2015157891 A1 | 10/2015 |
| WO | WO-2015157893 A1 | 10/2015 |
| WO | WO-2015157901 A1 | 10/2015 |
| WO | WO-2015165081 A1 | 11/2015 |
| WO | WO-2015180071 A1 | 12/2015 |
| WO | WO-2015184590 A1 | 12/2015 |
| WO | WO-2015184620 A1 | 12/2015 |
| WO | WO-2015192337 A1 | 12/2015 |
| WO | WO-2015196395 A1 | 12/2015 |
| WO | WO-2016000136 A1 | 1/2016 |
| WO | WO-2016000139 A1 | 1/2016 |
| WO | WO-2016000232 A1 | 1/2016 |
| WO | WO-2016000233 A1 | 1/2016 |
| WO | WO-2016015712 A1 | 2/2016 |
| WO | WO-2016023176 A1 | 2/2016 |
| WO | WO-2016029386 A1 | 3/2016 |
| WO | WO-2016029389 A1 | 3/2016 |
| WO | WO-2016082479 A1 | 6/2016 |
| WO | WO-2016149942 A1 | 9/2016 |
| WO | WO-2016165063 A1 | 10/2016 |
| WO | WO-2016172867 A1 | 11/2016 |
| WO | WO-2016187695 A1 | 12/2016 |
| WO | WO-2016187803 A1 | 12/2016 |
| WO | WO-2016201606 A1 | 12/2016 |
| WO | WO-2017007252 A1 | 1/2017 |
| WO | WO-2017015794 A1 | 2/2017 |
| WO | WO-2017034597 A1 | 3/2017 |
| WO | WO-2017049653 A1 | 3/2017 |
| WO | WO-2017054424 A1 | 4/2017 |
| WO | WO-2017070871 A1 | 5/2017 |
| WO | WO-2017097172 A1 | 6/2017 |
| WO | WO-2017102633 A1 | 6/2017 |
| WO | WO-2017102969 A1 | 6/2017 |

\* cited by examiner

VAPORIZER

CROSS REFERENCE TO RELATED APPLICATIONS

This application claims the benefit of U.S. Provisional Application Ser. No. 62/433,000, filed Dec. 12, 2016 and U.S. Provisional Application Ser. No. 62/485,195, filed Apr. 13, 2017, the disclosures of each of which are hereby incorporated herein by reference in their entireties.

BACKGROUND

1. Technical Field Text

This disclosure relates generally to vaporizers, and more particularly to a high capacity vaporizer and vapor storage system.

2. Background Information

Vaporizers have recently emerged as a new product for providing nicotine and other products through a smokeless inhalation process. There are many embodiments of vaporizers including the electronic cigarette. Most implementations consist of a power supply (typically a battery) and an atomizing device. In reusable electronic cigarettes the two items are separated into a battery and a cartomizer, to allow the disposal and replacement of the nicotine containing fluid cartomizer while preserving the more costly battery and associated circuitry (microcontroller, switch, indicating LED, etc.) In disposable electronic cigarettes the two items are combined to integrate the functions into one unit that is disposed of after either the battery energy or the nicotine containing E-liquid or other vaporizable material is exhausted.

The E-liquid or other vaporizable material that is used to produce vapor in electronic cigarettes is generally a solution of one or more of propylene glycol (PG) and/or vegetable glycerin (VG) and/or polyethylene glycol 400 (PEG400) mixed with concentrated flavors, and optionally, a variable percentage of a liquid nicotine concentrate. This liquid may be termed an "E-liquid" and is often sold in a bottle or in disposable cartridges or cartomizers. Many different flavors of such E-liquids are sold, including flavors that resemble the taste of regular tobacco, menthol, vanilla, coffee, cola and various fruits. Various nicotine concentrations are also available, and nicotine-free E-Liquids are common.

BRIEF SUMMARY

In one aspect of the disclosure, a vaporizer has a body, an air pump, a heating block, a filling chamber, an air channel, a battery, and a control panel. The body has an outer surface, an outlet through the outer surface, and an inlet through the outer surface. The air pump is disposed within the body and is in fluid communication with the inlet. The heating block is disposed within the body and is in fluid communication with the air pump. The filling chamber is disposed within the body and is in fluid communication with the heating block. The air channel passes through the heating block from the air pump and is in fluid communication with the outlet. The battery disposed within the body and the control panel is in electrical communication with the battery, the air pump, and the heating block. The control panel is configured to control a speed of the air pump and a temperature of the heating block.

DETAILED DESCRIPTION

The following detailed description and the appended drawings describe and illustrate some embodiments of the disclosure for the purpose of enabling one of ordinary skill in the relevant art to make and use these embodiments. As such, the detailed description and illustration of these embodiments are purely illustrative in nature and are in no way intended to limit the scope of the disclosure in any manner. It should also be understood that the drawings are not necessarily to scale and in certain instances details may have been omitted, which are not necessary for an understanding of the embodiments, such as details of fabrication and assembly. In the accompanying drawings, like numerals represent like components.

Figure 1:
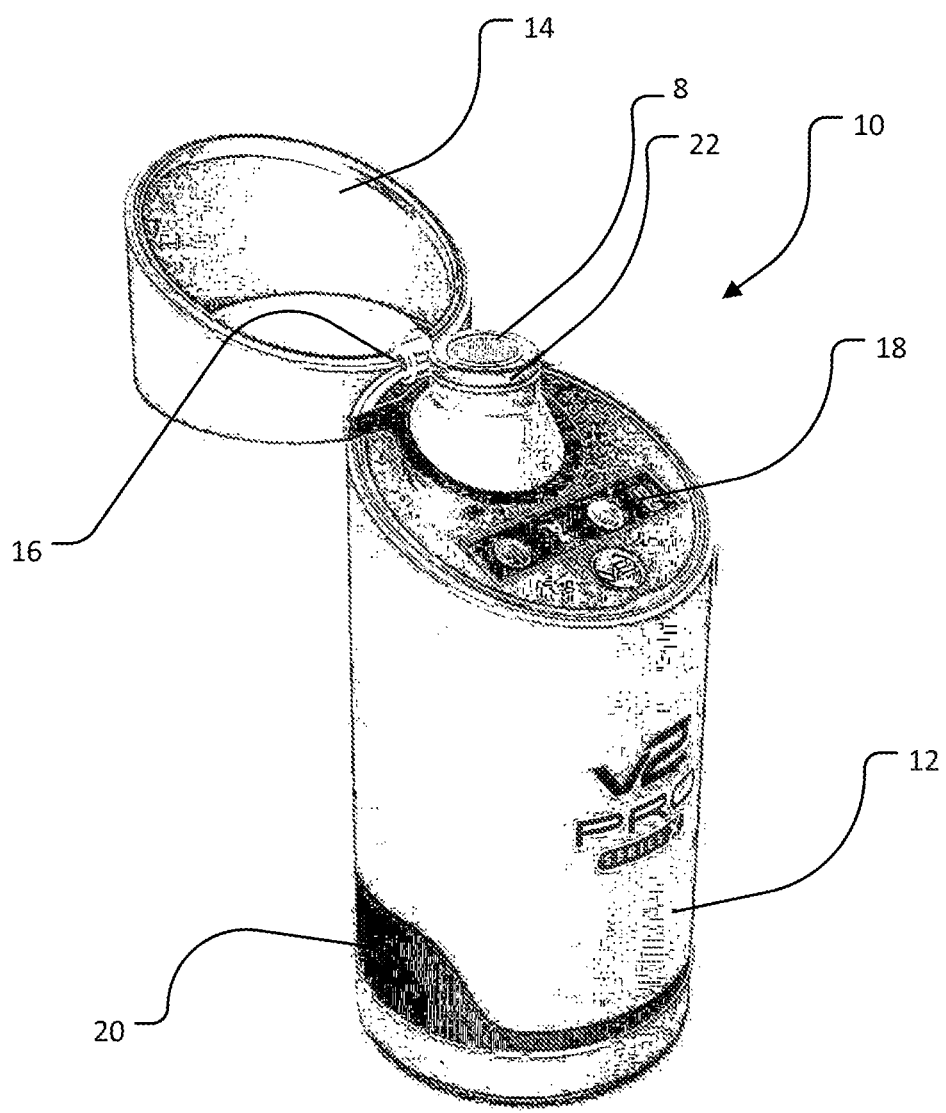
FIG. 1 illustrates a perspective view of an embodiment of a vaporizer.

FIG. 1 illustrates an embodiment of a vaporizer 10. In contrast to a traditional vaporizer, vaporizer 10 has a greater vaporizing capacity. Vaporizer 10 includes a body 12 housing internal components and a lid 14. Hinge 16 attaches lid 14 to body 12. Body 12 includes a control panel 18 for operation of vaporizer 10, controlling functions such as power, temperature control, air volume, and duration. Vaporizer 10 draws air through an inlet 20 and expels a combination of air and vapor through an outlet 22. Outlet 22 may further include a screen 8 over the mouth of the outlet's opening (vapor exit). Use of screen 8 may assist in knocking down large vapor droplets or solid vaporizable material carried from the atomizer with the vapor/air mixture, thus maintaining a more consistent vapor stream, while reducing or preventing potential for leakage or loss of non-vaporized material.

Figure 2:
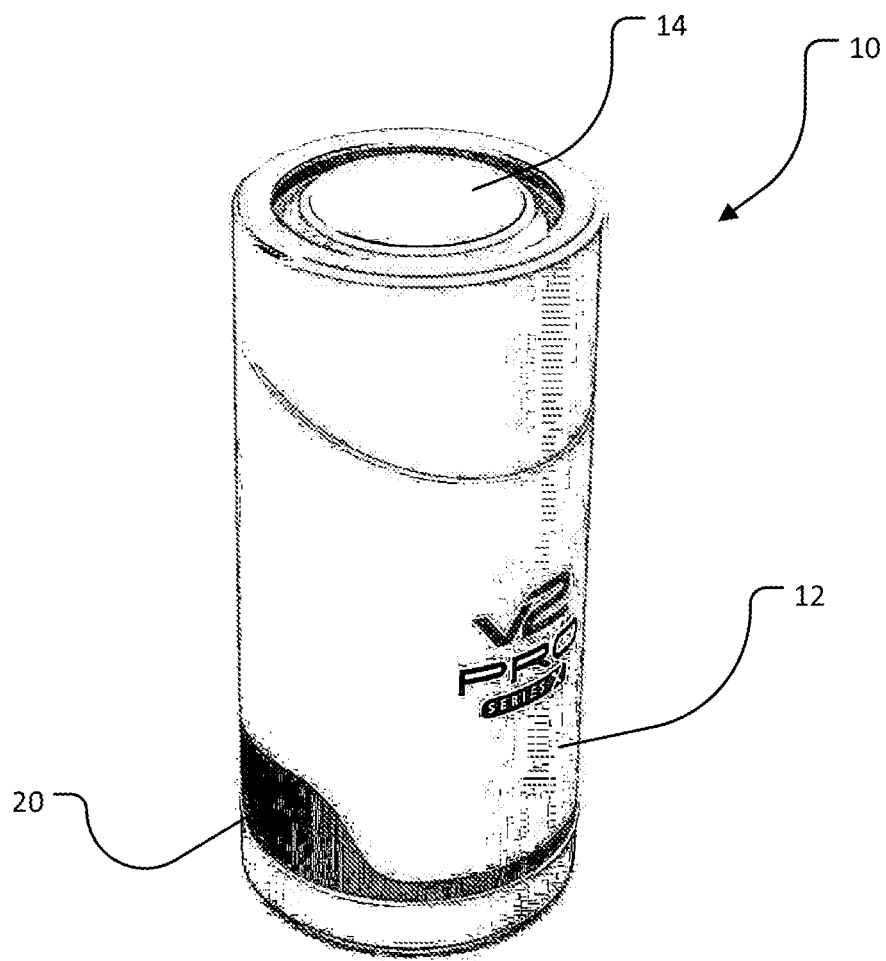
FIG. 2 illustrates another view of the vaporizer of FIG. 1.

FIG. 2 illustrates vaporizer 10 of FIG. 1, but with lid 14 in a closed configuration. Lid 14 protects outlet 22 and control panel 18 when in the closed configuration. Vaporizer 10 may include a sensor to detect when lid 14 is open or closed. When closed, vaporizer 10 may be powered off, or in a low power stand-by mode. Opening lid 14 may cause vaporizer 10 to power on.

Figure 3:
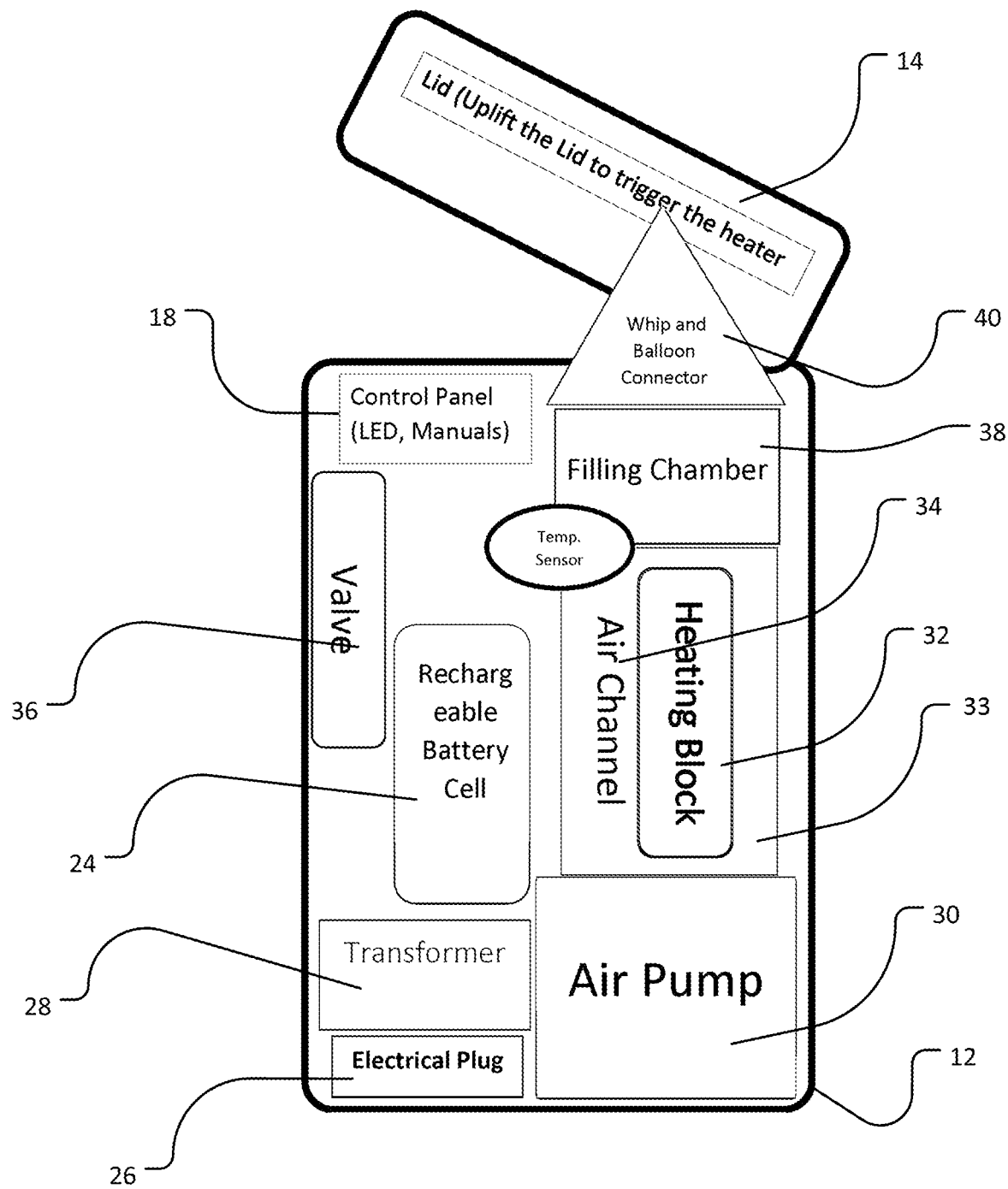
FIG. 3 illustrates a schematic of components in an embodiment of a vaporizer.

FIG. 3 illustrates a schematic view of the components contained within body 12. Vaporizer 10 may be powered using an internal battery 24, or may use an external power source such as an external battery or a power adapter plugged into a power source through electrical plug 26. A power supply 28 (for example, transformer) may be contained within vaporizer 10 to convert external voltage sources to a voltage suitable for use by vaporizer 10.

Power supply 28 is electrically coupled to control panel 18, which controls a supply of electrical power to an air pump 30 and a heating block 32. Air pump 30 draws ambient air through inlet 20 and expels the air through an air channel 34 in the heating block 32. Heating block 32 heats a product such as E-liquid or other vaporizable material in heating chamber 33 to create vapor. The air mixes with the vapor before being exhausted from vaporizer 10 through outlet 22. Air pump 30 allows for the production of vapor product without requiring a user to draw air through the vaporizer 10. In a traditional vaporizer such as an E-cigarette, a user inhales, drawing air through the E-cigarette to mix with vapor. Air pump 30 replaces the user, allowing vaporizer 10 to deliver vapor using other delivery methods.

A valve 36 may be controlled by the LED panel 18 to adjust the amount of air delivered by the air pump 30. In some embodiments, valve 36 may control the flow of product to heating block 32. In some embodiments, one or more valves 36 may control the supply of air and the flow of product. The valves may be adjusted manually, or may be operated by control panel 18.

A filling chamber 38 is contained within body 12 and has a tank for housing E-liquid or other vaporizable material. Filling chamber 38 is in fluid communication with heating block 32 and delivers a controlled amount of E-liquid or other vaporizable material to the heating block 32 for vaporization. The flow of E-liquid or other vaporizable material may be controlled by valve 36 in some embodiments, or it may be controlled by the rate at which E-liquid or other vaporizable material is vaporized in the heating block 32. The E-liquid or other vaporizable material flows into heating block 32 and is vaporized by heating the E-liquid. The resulting vapor is mixed with air from air channel 34 in heating chamber 33 to form an inhalable product.

The inhalable vaporized material travels from air channel 34 to an outlet 22, normally concealed by cover 14 or other lid. In some embodiments, control panel 18 may be configured to cause heating block 32 to heat the E-liquid or other vaporizable material in response to cover 14 being lifted. Alternatively, in other embodiments, heating block 32 may be inactive whenever cover 14 is in place and unlocks for activation only after cover 14 has been lifted.

Beneath cover 14 is outlet 22, which may receive various types of connectors for coupling outlet 40 to different types of vapor delivery devices. In some embodiments, a connector may be sized and shaped to connect outlet 22 to flexible tubes known as whips. In some embodiments, the connector 40 may couple outlet 22 to multiple whips. In other embodiments, the connector 40 may connect to device for storage of vapor, such a balloon.

Figure 4:
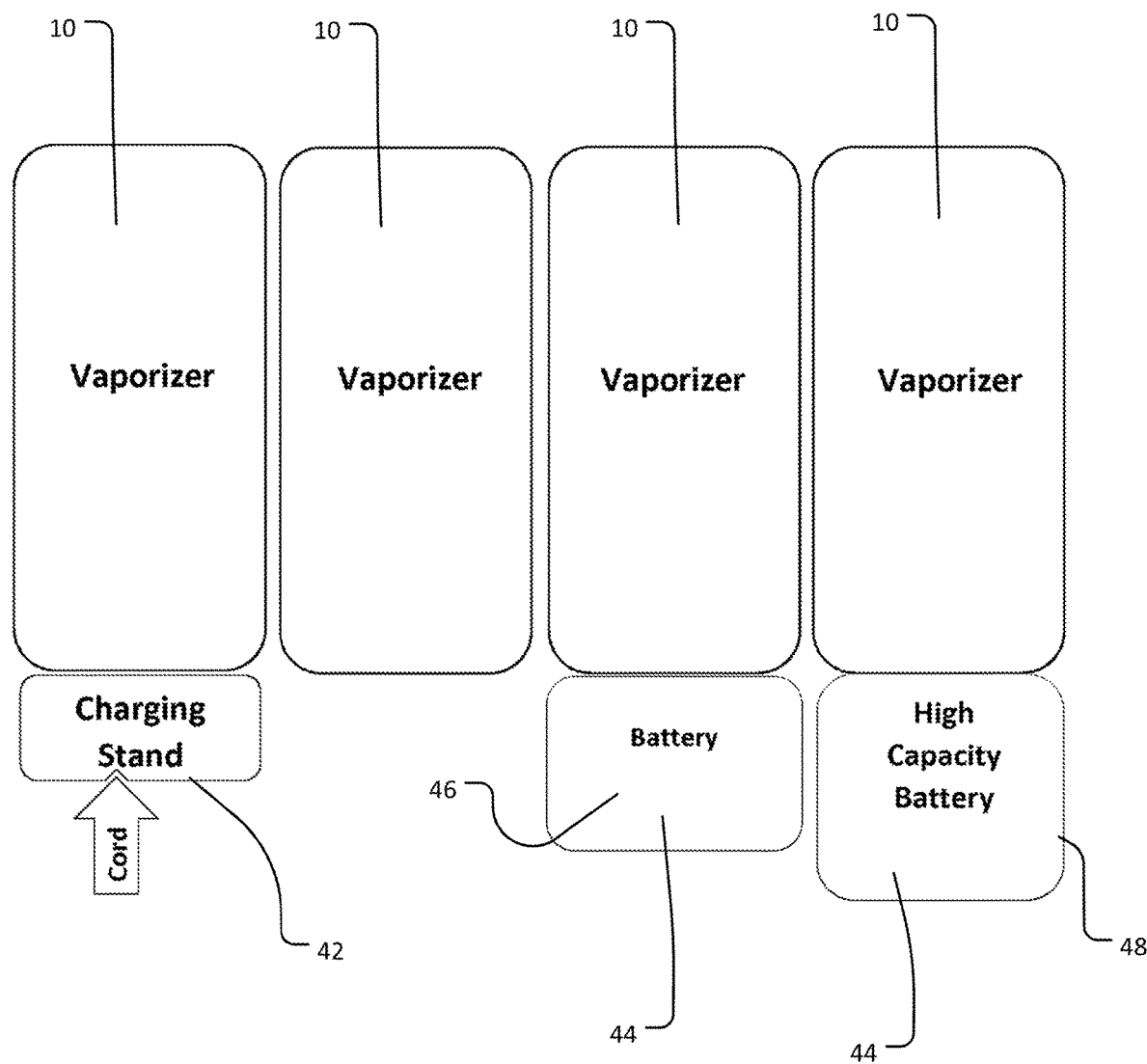
FIG. 4 illustrates a schematic of various configurations of powering a vaporizer.

FIG. 4 illustrates a schematic diagram of an embodiment of a vaporizer 10. Vaporizer 10 has an internal battery for powering the heating block 32 for vaporizing E-liquid. In addition to the internal battery 24, vaporizer 10 may be powered using other techniques. In some embodiments, vaporizer 10 may have an external charging stand 42. External charging stand 42 may plug into an electrical outlet to receive power. The power is then delivered to the vaporizer 10 to charge the internal battery 24 and/or power the vaporizer 10. The charging stand 42 may provide power to the vaporizer 10 using common techniques such as a wired plug, a wireless inductive coupling, electrical contacts, etc. Vaporizer 10 may be charged in response to vaporizer 10 being placed on the stand 42.

In another embodiment, an external battery 44 may be utilized to power the device and/or charge the internal battery 24. The external battery 44 may be a standard capacity battery 46, or may be an extended life, high capacity battery 48. Like charging stand 42, external batteries 44 may be electrically coupled to vaporizer 10 using common techniques such as plugs, inductive couplings, and electrical contacts. In addition to the electrical coupling, external batteries 44 may be physically coupled to the vaporizer 10 such that that they may be moved as a single unit. For instance, external battery 44 may have a twist lock connection to vaporizer 10, securing vaporizer 10 and external battery 44 together in a single unit.

Figure 5:
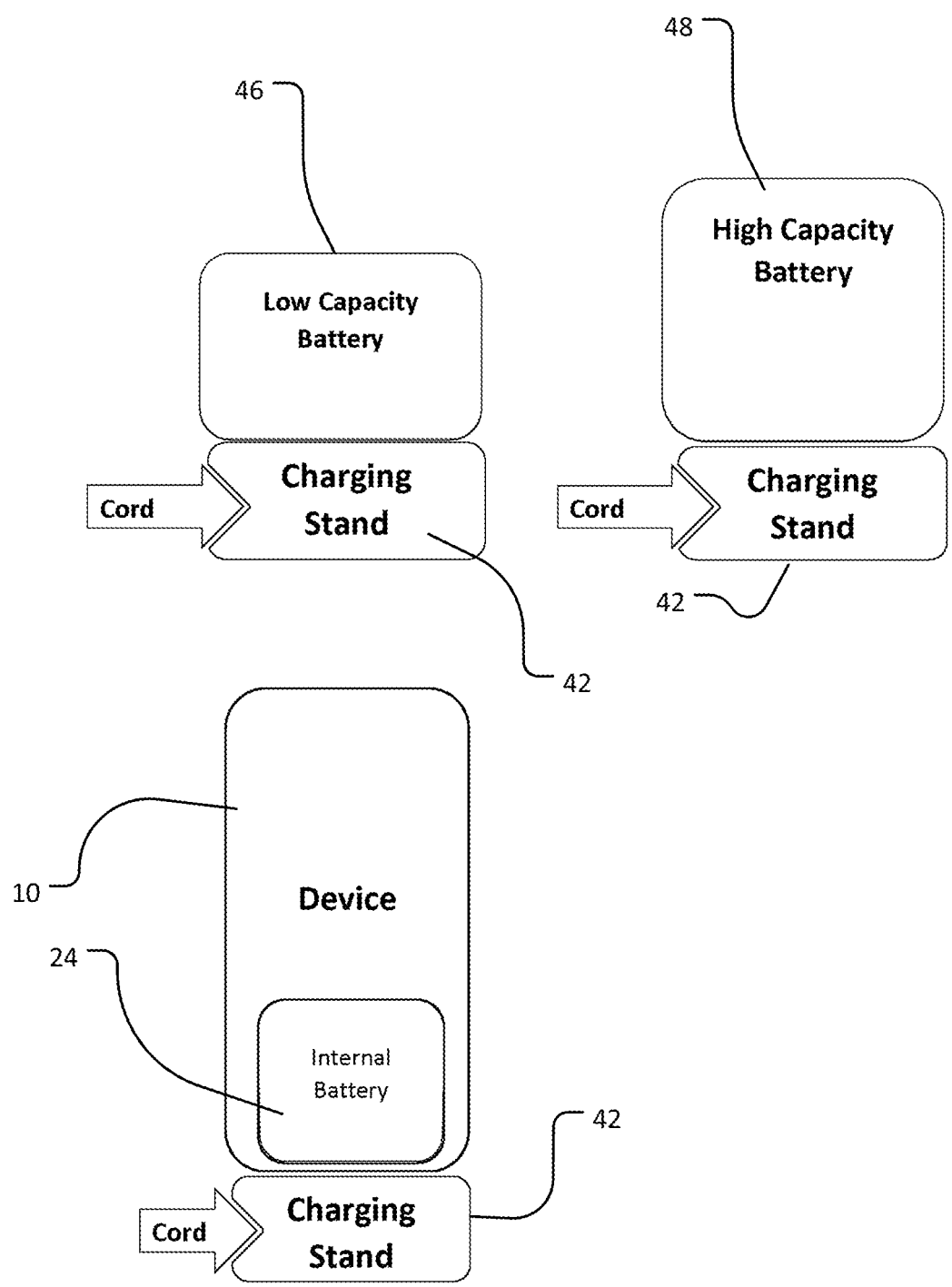
FIG. 5 illustrates a schematic of various charging configurations for a vaporizer.

FIG. 5 illustrates a diagram of charging stand 42 as used with vaporizer 10 and associated external batteries 44. In one embodiment, charging stand 42 is coupled directly to low capacity battery 46 for charging. In another embodiment, charging stand 42 is coupled directly to high capacity battery 48 for charging. Batteries 44 may charge independent of vaporizer 10 as shown in the upper portion of FIG. 5. In some embodiments, vaporizer 10 may be coupled to external battery 44 battery while it is being charged. If no external battery 44 is present, vaporizer 10 may be placed directly on charging stand 42 to charge internal battery 24.

Figure 6:
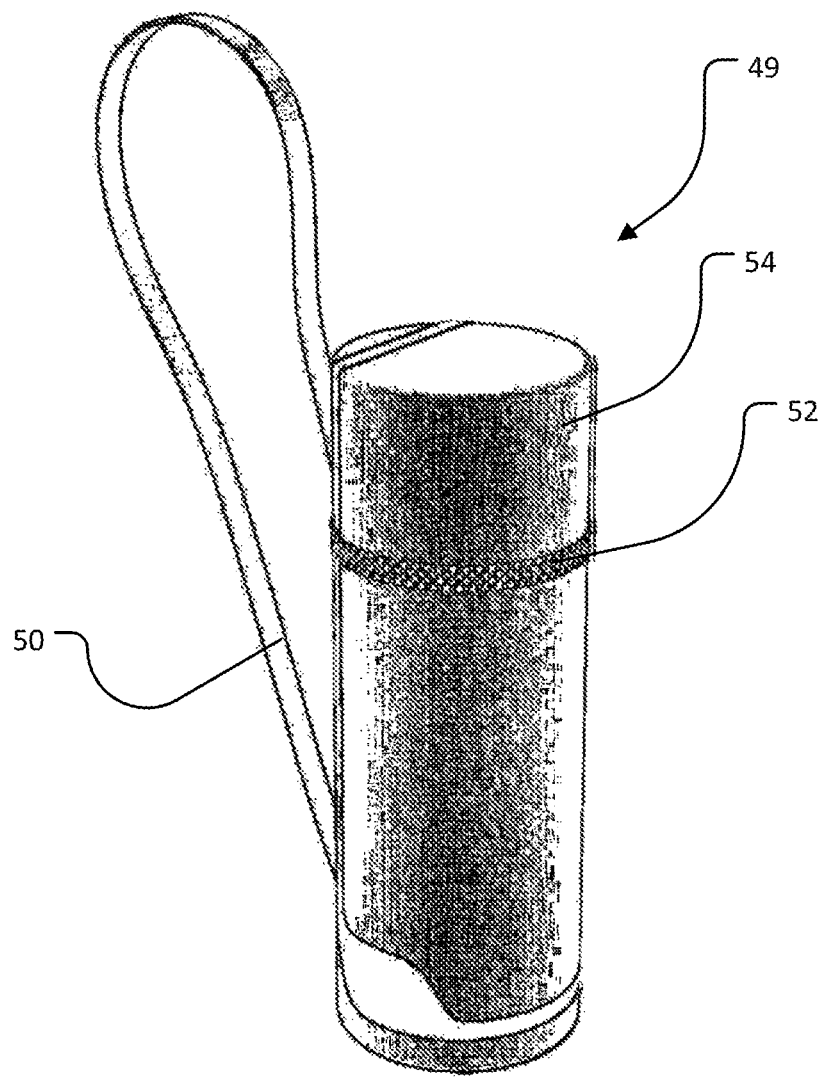
FIG. 6 illustrates a vaporizer contained in a portable case.

FIG. 6 illustrates an embodiment of a case 49 for transporting a vaporizer 10. A strap 50 may be attached to case 49 as a means to carry vaporizer 10 when not in use. A releasable fastener, such as a zipper 52, may selectively couple cover 54 to case 49. During use, zipper 52 may be undone allowing cover 54 to be removed from case 49.

Figure 7:
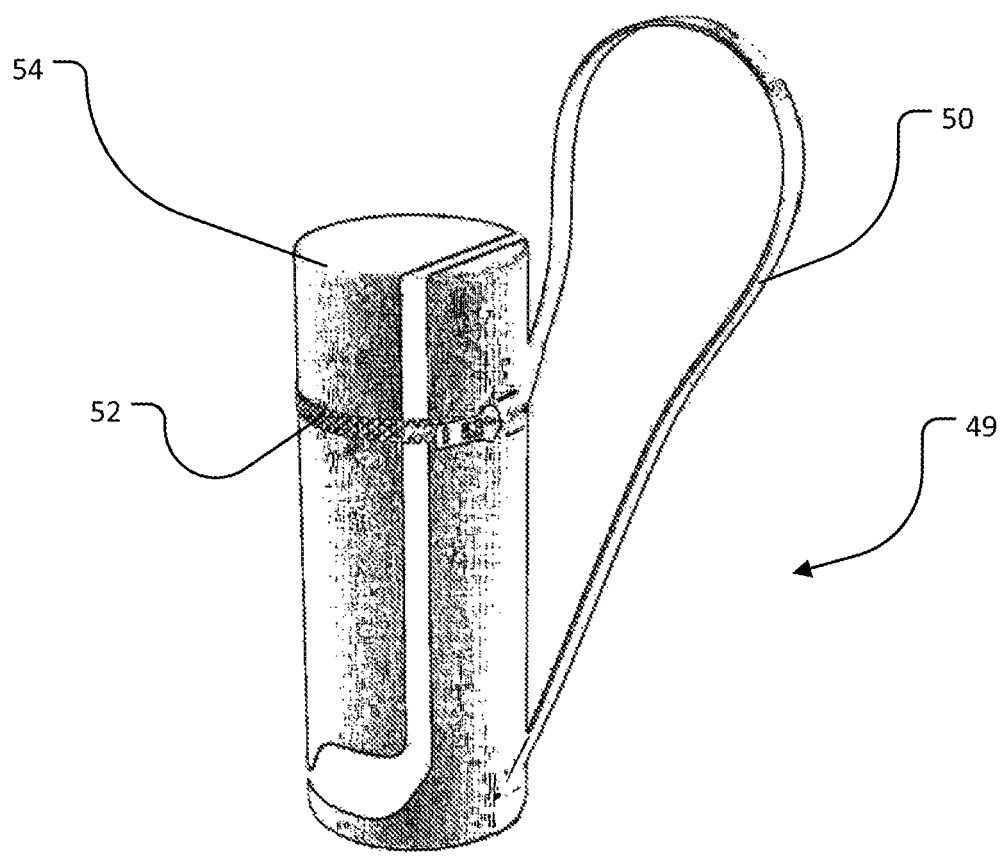
FIG. 7 illustrates another view of vaporizer contained in a portable case.
Figure 8:
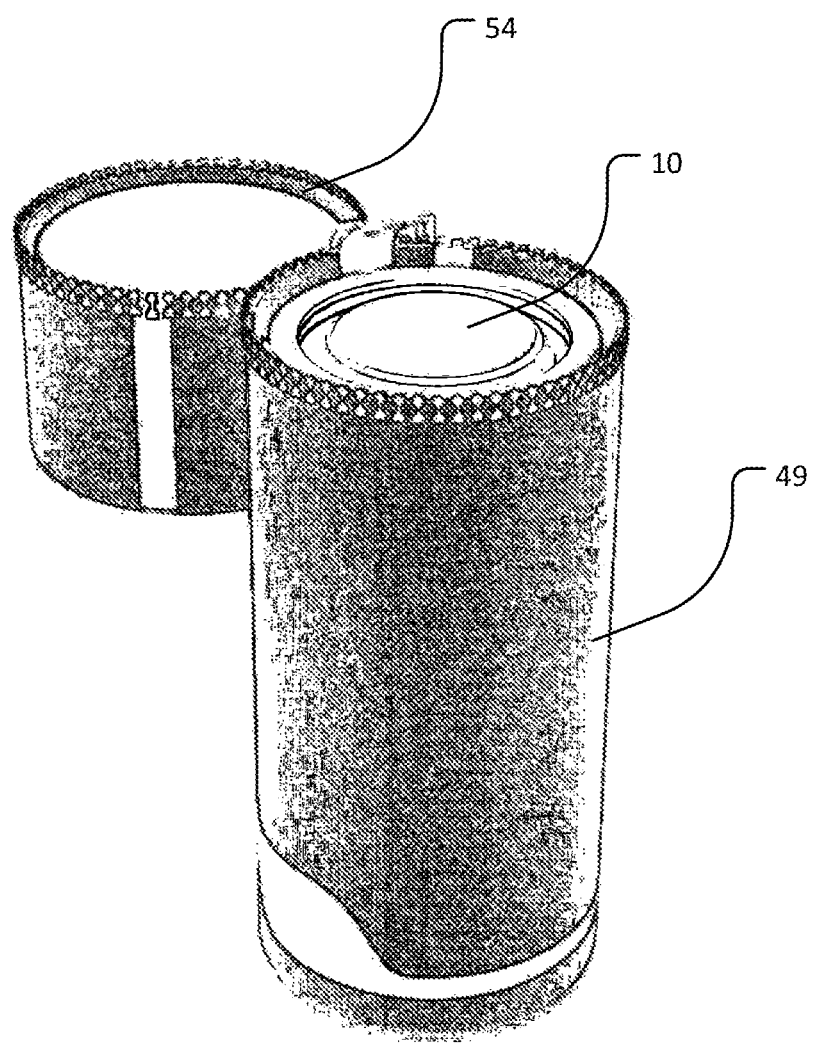
FIG. 8 illustrates another view of a vaporizer in a portable case with a cover removed.
Figure 9:
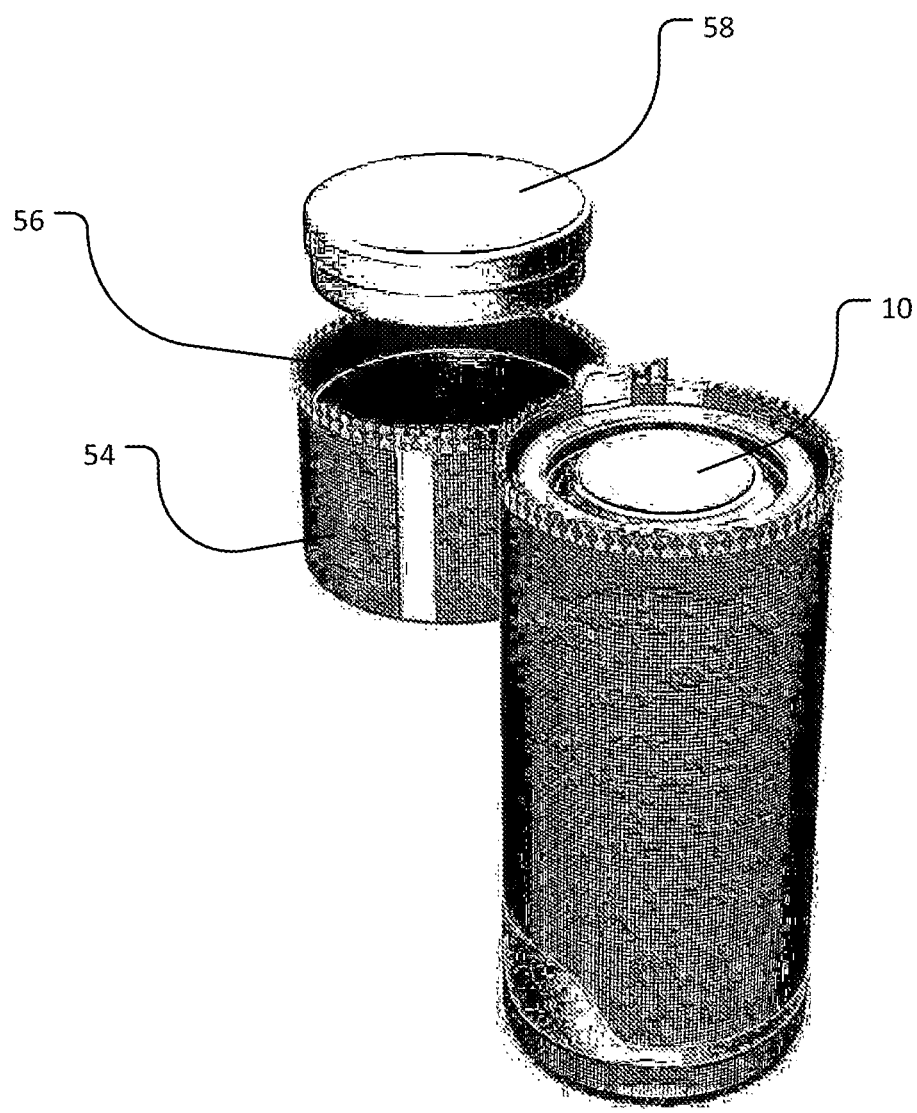
FIG. 9 illustrates another view of a vaporizer in a portable case showing a storage pocket.

FIG. 7 illustrates an alternate view of the embodiment of case 49 for transporting vaporizer 10. This alternate view shows strap 50 and zipper 52 fastening cover 54 to case 49. FIG. 8 illustrates an embodiment of case 49 with cover 54 removed to reveal vaporizer 10. In some embodiments, cover 54 may have a sealable cavity 56 as shown in FIG. 9. The sealable cavity 56 may hold product for producing vapor, a spare battery, a charging stand, or other component for use with vaporizer 10. In some embodiments, the cavity may have a cap 58 sealing the contents of cavity 56. Cap 58 may have threads that screw into complementary threads on cover 54.

Figure 10:
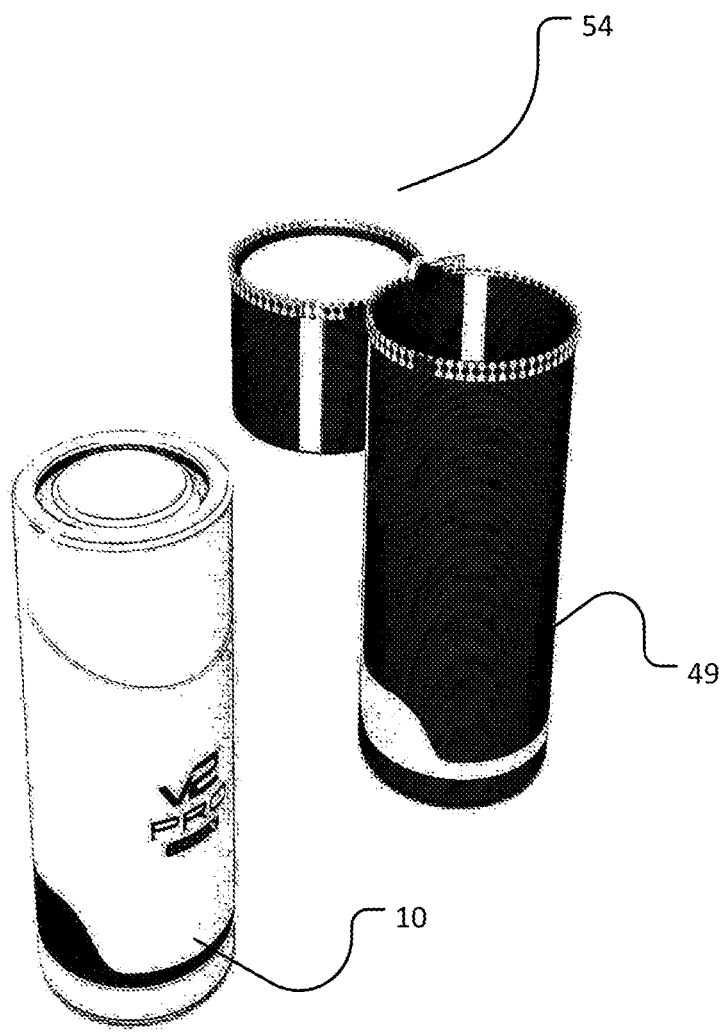
FIG. 10 illustrates the vaporizer separate from the portable case.

FIG. 10 illustrates vaporizer 10 standing next to case 49. Vaporizer 10 may be inserted into case 49 for transportation and protection. In some embodiments, case 49 may include cutouts at a base end that align with cutouts at a base end of vaporizer 10. Vaporizer 10 may be charged using the charging stand 42 by inserting a charging cable or other charging device through the cutouts to couple to vaporizer 10. In embodiments using an inductive coupling, the base of case 49 may be transparent to the power coupling and charged by setting vaporizer 10 on the charging stand 10.

Figure 11:
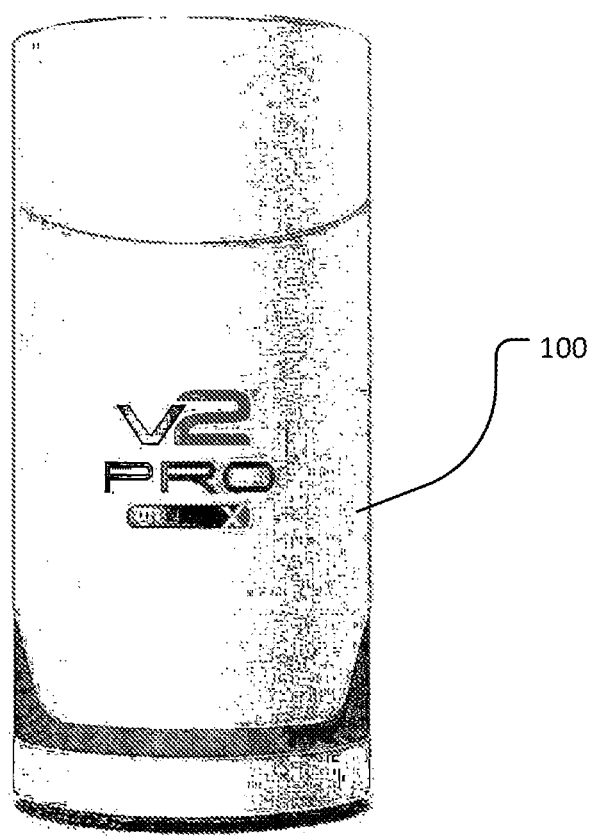
FIG. 11 illustrates a side view of the vaporizer.
Figure 12:
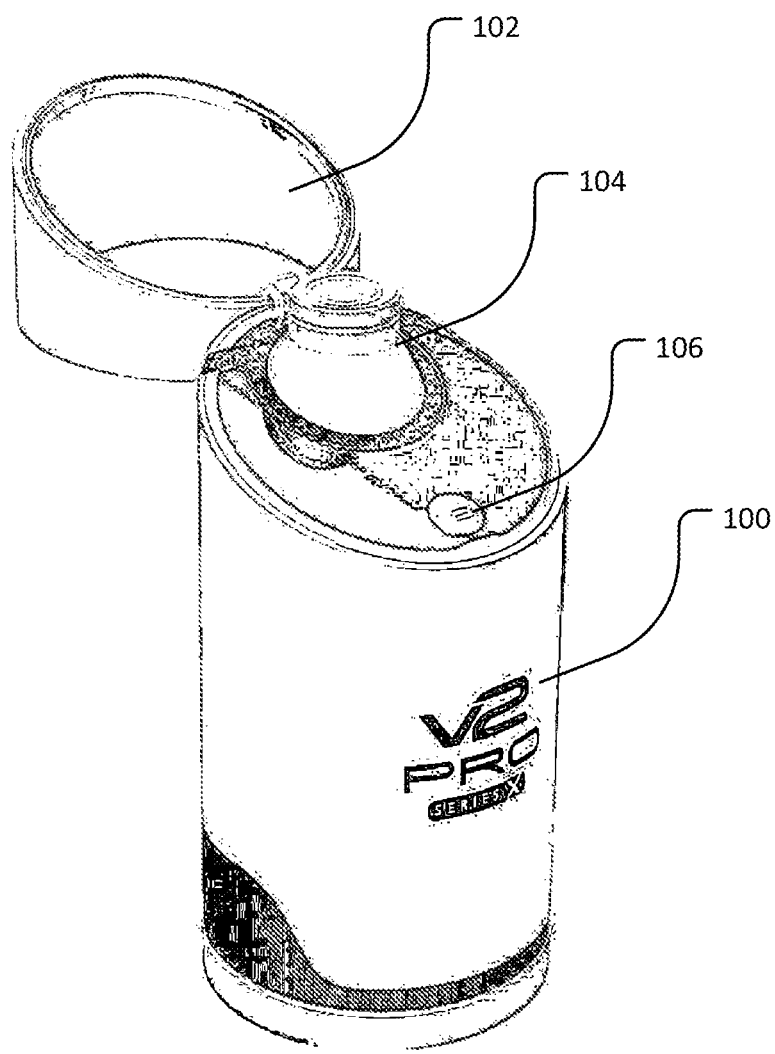
FIG. 12 illustrates a perspective view of the vaporizer with a cap removed.

FIG. 11 illustrates a front view of an alternative embodiment of vaporizer 100. FIG. 12 illustrates vaporizer 100, having a lid 102 opened to expose an outlet 104 of the vaporizer 100. The embodiment of FIG. 12 is substantially similar to the previously described embodiment, with the exception that it has a single control button 106 in place of the control panel. The control button 106 may be pressed to activate a heating chamber to produce vapor.

Figure 13:
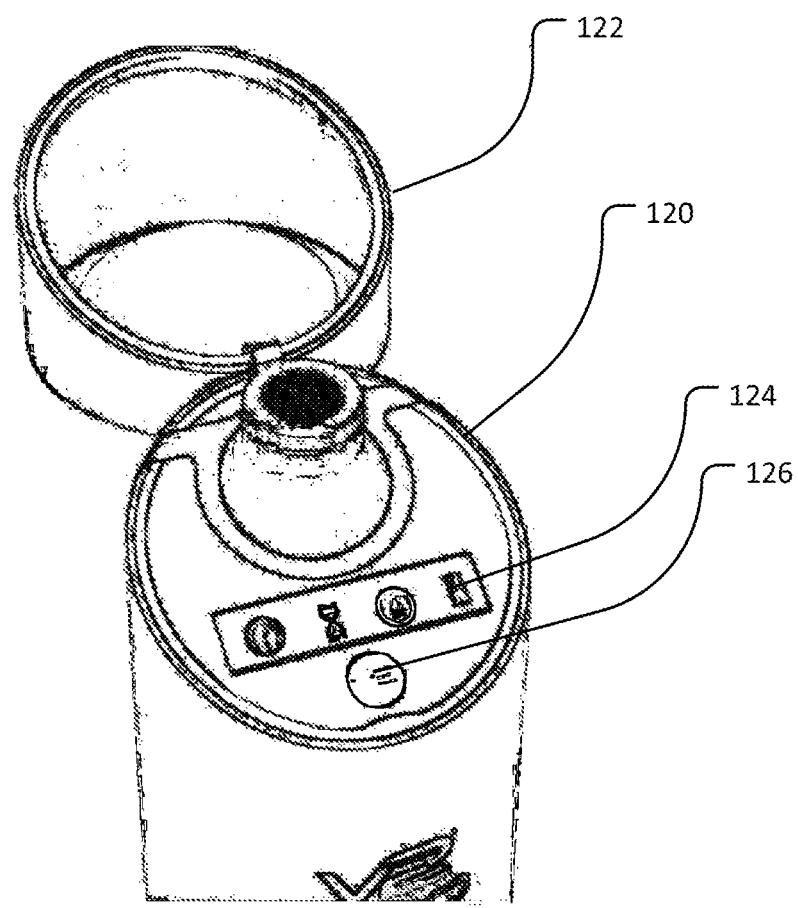
FIG. 13 illustrates an upper portion of the vaporizer.

FIG. 13 illustrates an embodiment of a vaporizer 120 with a lid 122 removed to expose control panel 124. Control panel 124 gives visual indications of the status of the vaporizer 120. Control panel 124 may indicate features such as remaining battery power, estimated battery life, and temperature of heating chamber. Control panel 124 may be interactive such as by way of a touch screen. The embodiment of FIG. 13 further includes a button 126 for operation of the vaporizer. Button 126 may function similarly to the button of FIG. 11, or its functionality may interact with the control panel display 124. In some embodiments, pressing button 126 may cause the vaporizer 120 to begin producing vapor from an E-liquid.

Figure 14:
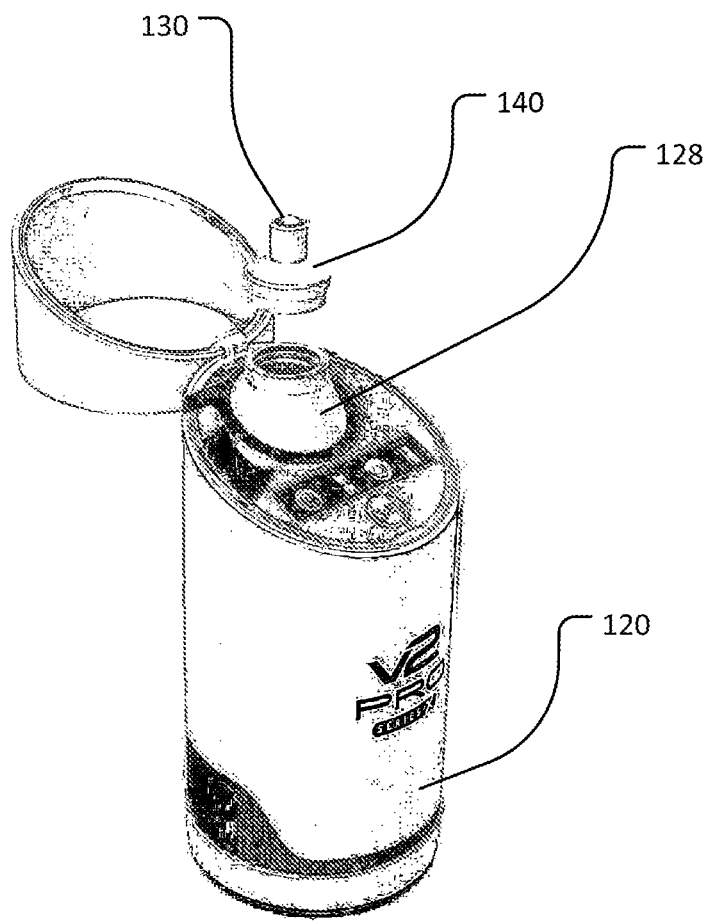
FIG. 14 illustrates the vaporizer with a removable outlet adapter.

FIG. 14 illustrate the embodiment of FIG. 13 with a connector 140 for connecting outlet 128 to a vapor storage device or whip. Connector 140 is secured within outlet 128 and has a portion 130 configured to connect to an accessory. For example, a whip may fit over the reduced diameter portion 130 of connector 140 and be secured by friction. Or a balloon device may fit over the reduced diameter portion 130 for receiving vapor.

Figure 15:
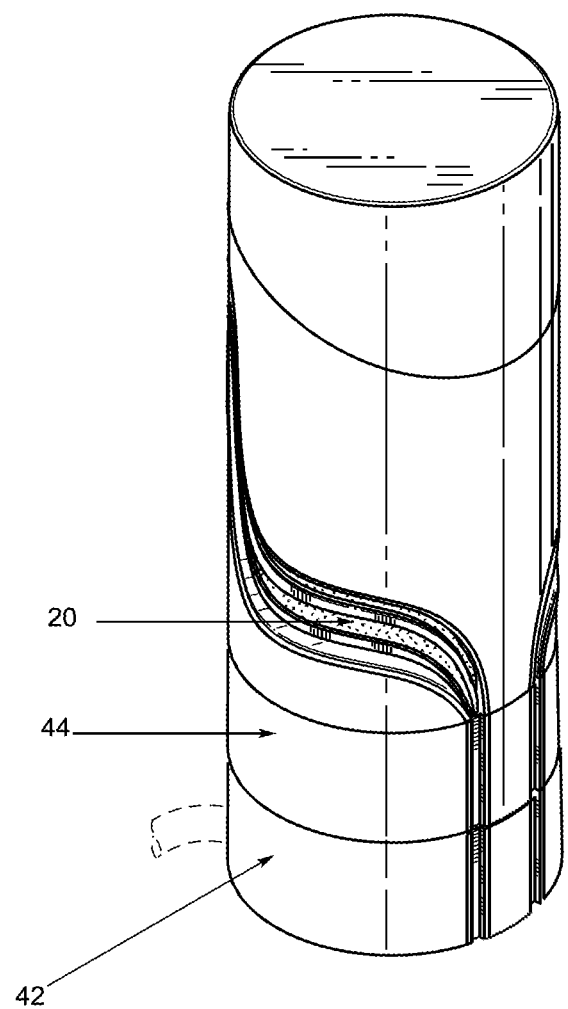
FIG. 15 illustrates a perspective view of a vaporizer in contact with an external battery and charging stand.

FIG. 15 illustrates an embodiment of the disclosure wherein the vaporizer, battery and charger may be configured to allow operation of the vaporizer during the time that the battery is being charged.

Some embodiments of the present disclosure are directed to vaporizer kits comprising a vaporizer as described herein and instructions for operating the vaporizer. In some embodiments, the kit further comprises a carrying case. In other embodiments, the vaporizer further comprises at least one connector for coupling to a vapor delivery device. In other kit embodiments having at least one connector, at least one connector is configured to couple to a flexible tube. In yet other embodiments, the vapor delivery device being connected to the vaporizer is a balloon.

The descriptions set forth above are meant to be illustrative and not limiting. Various modifications of the invention, in addition to those described herein, will be apparent to those skilled in the art from the foregoing description. Such modifications are also intended to fall within the scope of the concepts described herein. The disclosures of each patent, patent application and publication cited or described in this document are hereby incorporated herein by reference, in their entireties.

The foregoing description of possible implementations consistent with the present disclosure does not represent a comprehensive list of all such implementations or all variations of the implementations described. The description of some implementation should not be construed as an intent to exclude other implementations. For example, artisans will understand how to implement the invention in many other ways, using equivalents and alternatives that do not depart from the scope of the invention. Moreover, unless indicated to the contrary in the preceding description, none of the components described in the implementations are essential to the invention. It is thus intended that the embodiments disclosed in the specification be considered as illustrative, with a true scope and spirit of the invention being indicated by the following claims.

The invention claimed is:

1. A vaporizer, comprising:
a body having an outer surface, an outlet through the outer surface, and an inlet through the outer surface;
an air pump disposed within the body, the air pump being in fluid communication with the inlet;
a heating block disposed within the body, the heating block in fluid communication with the air pump;
a filling chamber disposed within the body, the filling chamber in fluid communication with the heating block;
an air channel passing through the heating block from the air pump and in fluid communication with the outlet;
a battery disposed within the body;
a control panel in electrical communication with the battery, the air pump, and the heating block, wherein the control panel configured to control a speed of the air pump and a temperature of the heating block;
a lid connected to the body by a hinge coupled to the outer surface of the body, the lid movable about the hinge between an open position and a closed position, wherein the lid covers the outlet and the control panel when the lid is in the closed position; and
a sensor configured to detect whether the lid is in the open position or in the closed position,
wherein the vaporizer is configured to enter a power-on mode when the lid is in the open position, and wherein the vaporizer is configured to enter a power-off mode when the lid is in the closed position.

2. The vaporizer according to claim 1, further comprising a valve in electrical connection with the control panel, the valve configured to adjust the amount of air delivered by the air pump.

3. The vaporizer according to claim 1, further comprising a heating chamber in electrical communication with the control panel or a control button, the heating chamber configured to heat vaporizable material to a vaporization temperature.

4. The vaporizer according to claim 1, wherein the outlet further comprises a screen.

5. A kit comprising a vaporizer according to claim 1 and instructions for operating the vaporizer.

6. The kit according to claim 5, further comprising a carrying case.

7. The kit according to claim 5, further comprising at least one connector for coupling to a vapor delivery device.

8. The kit according to claim 7, wherein the at least one connector is configured to couple to a flexible tube.

9. The kit according to claim 7, wherein the vapor delivery device is a balloon.

10. A vaporizer, comprising:
a body having an outer surface, an outlet through the outer surface, and an inlet through the outer surface;
an air pump disposed within the body, the air pump being in fluid communication with the inlet;
a heating block disposed within the body, the heating block in fluid communication with the air pump;
a filling chamber disposed within the body, the filling chamber in fluid communication with the heating block;
an air channel passing through the heating block from the air pump and in fluid communication with the outlet;
a battery disposed within the body;
a control panel in electrical communication with the battery, the air pump, and the heating block, the control panel configured to control a speed of the air pump and a temperature of the heating block; and
a lid coupled to the outer surface of the body and movable between an open position and a closed position, wherein the lid covers the outlet and the control panel when the lid is in the closed position, wherein the vaporizer is configured to enter a power-on mode when the lid is in the open position, and wherein the vaporizer is configured to enter a power-off mode when the lid is in the closed position.

11. The vaporizer according to claim 10, wherein the lid is coupled to the outer surface of the body by a hinge.

12. The vaporizer according to claim 10, further comprising a sensor configured to detect whether the lid is in the open position or in the closed position.

13. The vaporizer according to claim 10, wherein the battery is configured to be charged by wireless inductive coupling in response to being placed on a charging stand.

14. The vaporizer according to claim 10, further comprising an external battery configured to charge the battery.

* * * * *